US010092695B2

(12) United States Patent
Ilan et al.

(10) Patent No.: US 10,092,695 B2
(45) Date of Patent: Oct. 9, 2018

(54) ADDITION TO A MEDICAL APPLICATOR

(71) Applicants: Omrix Biopharmaceuticals Ltd., Rehovot (IL); Ethicon, Inc., Somerville, NJ (US)

(72) Inventors: Erez Ilan, Kibbutz Netzer Sereni (IL); Kfir Regev, Tel-Aviv (IL); Yotam Gurman, Kibbutz or Haner (IL); Robert J. Tannhauser, Bridgewater, NJ (US)

(73) Assignees: Ethicon, Inc., Somerville, NJ (US); Omrix Biopharmaceuticals Ltd., Rehovot (IL)

( * ) Notice: Subject to any disclaimer, the term of this patent is extended or adjusted under 35 U.S.C. 154(b) by 30 days.

(21) Appl. No.: 14/848,534

(22) Filed: Sep. 9, 2015

(65) Prior Publication Data

US 2016/0074579 A1 Mar. 17, 2016

Related U.S. Application Data

(60) Provisional application No. 62/048,925, filed on Sep. 11, 2014.

(30) Foreign Application Priority Data

Sep. 11, 2014 (IL) .......................................... 234607

(51) Int. Cl.

| | |
|---|---|
| ***A61M 39/00*** | (2006.01) |
| ***A61M 5/162*** | (2006.01) |
| ***A61B 17/00*** | (2006.01) |
| ***A61M 5/28*** | (2006.01) |
| ***A61M 13/00*** | (2006.01) |

(52) U.S. Cl.

CPC ....... *A61M 5/162* (2013.01); *A61B 17/00491* (2013.01); *A61M 5/284* (2013.01); *A61M 13/00* (2013.01); *A61B 2017/00495* (2013.01); *A61M 5/288* (2013.01); *A61M 39/00* (2013.01); *A61M 2039/0027* (2013.01)

(58) Field of Classification Search

CPC ... A61B 17/00491; A61B 2017/00495; A61M 2039/0027; A61M 5/284

See application file for complete search history.

(56) References Cited

U.S. PATENT DOCUMENTS

| | | | |
|---|---|---|---|
| 369,767 | A | 9/1887 | Beall |
| 1,642,950 | A | 9/1927 | Haas |

(Continued)

FOREIGN PATENT DOCUMENTS

| | | | |
|---|---|---|---|
| EP | 1955727 | B1 | 2/2011 |
| EP | 2689796 | A1 | 1/2014 |

(Continued)

OTHER PUBLICATIONS

International Search Report re: PCT/IL2015/00041 dated Feb. 4, 2016.

(Continued)

*Primary Examiner* — Deanna K Hall

(74) *Attorney, Agent, or Firm* — David R. Crichton

(57) ABSTRACT

The presently disclosed subject matter relates to an addition to a medical applicator in general and in particular to an addition to a medical applicator for applying on a surface a curable liquid substance having multi components.

11 Claims, 5 Drawing Sheets

(56) References Cited

U.S. PATENT DOCUMENTS

| | | | | |
|---|---|---|---|---|
| 5,810,885 | A | 9/1998 | Zinger | |
| 6,113,571 | A * | 9/2000 | Zinger | A61B 17/00491 604/191 |
| 6,458,095 | B1 | 10/2002 | Wirt et al. | |
| 6,699,229 | B2 | 3/2004 | Zinger et al. | |
| 7,455,248 | B2 | 11/2008 | Kablik et al. | |
| 7,946,417 | B2 | 5/2011 | Plishka et al. | |
| 7,951,108 | B2 | 5/2011 | Harper et al. | |
| 7,967,779 | B2 | 6/2011 | Bertron et al. | |
| 8,376,989 | B2 | 2/2013 | Rissman et al. | |
| 8,403,882 | B2 | 3/2013 | Goldberg | |
| 8,721,582 | B2 | 5/2014 | Ji | |
| 8,827,980 | B2 * | 9/2014 | Ji | A61M 13/00 604/500 |
| 2003/0040701 | A1 | 2/2003 | Dalmose | |
| 2003/0187408 | A1 * | 10/2003 | Marx | A61B 17/00491 604/236 |
| 2007/0191781 | A1 | 8/2007 | Richards et al. | |
| 2010/0219200 | A1 | 9/2010 | Plishka et al. | |
| 2011/0021982 | A1 | 1/2011 | Keller | |
| 2014/0207097 | A1 | 7/2014 | Ji | |

FOREIGN PATENT DOCUMENTS

| | | | |
|---|---|---|---|
| JP | 9182786 | A | 7/1997 |
| WO | WO 2010/095128 | A2 | 8/2010 |
| WO | WO 2011/092694 | A2 | 8/2011 |
| WO | WO 2012/146652 | A1 | 11/2012 |
| WO | WO 2012/168933 | A2 | 12/2012 |

OTHER PUBLICATIONS

International Preliminary Report re: PCT/IL2015/00041 dated Mar. 14, 2017.

* cited by examiner

ADDITION TO A MEDICAL APPLICATOR

TECHNOLOGICAL FIELD

The presently disclosed subject matter relates to a medical applicator in general and in particular to a medical applicator for applying on a surface a curable liquid substance having multi components.

BACKGROUND ART

References considered to be relevant as background to the presently disclosed subject matter are listed below:

U.S. Pat. No. 7,455,248; U.S. Pat. No. 8,721,582; U.S. Pat. No. 8,376,989 B2; U.S. Pat. No. 7,946,417 B2; U.S. Pat. No. 7,951,108 B2; U.S. Pat. No. 7,967,779 B2; U.S. Pat. No. 6,458,095 B1; U.S. Pat. No. 6,699,229 B2; JP9182786 A; U.S. Pat. No. 369,767; US20110021982 A1; US20100219200 A1; US20030040701 A1; WO2011/092694A2; U.S. Pat. No. 5,810,885; U.S. Pat. No. 1,642,950; EP2689796A1.

Acknowledgement of the above references herein is not to be inferred as meaning that these are in any way relevant to the patentability of the presently disclosed subject matter.

BACKGROUND

Medical treatments and procedures often entail applying medicaments on a surface. Such medicaments can be a composition comprising two or more components that for optimal results should not be mixed together until use.

U.S. Pat. No. 5,810,885 discloses a device for applying a multi-component fluid, such as medical tissue or dental adhesives. The device comprises a headpiece having channels for each fluid extending from an inlet side of the headpiece to a connection site of the headpiece. The device further includes a tubular body comprising an inlet end facing the connection site of the headpiece and an outlet end facing away from the inlet end.

FIG. 1 shows another known medical applicator 10 configured for applying a multicomponent medicament on a surface, for example, a curable liquid substance. The medical applicator 10 includes a headpiece (also referred to as manifold) 12 having an outlet port 14 to which a tubular body 15 is coupled, and two or more cannulas 16*a* and 16*b* into which the components can be fed. Each of the cannulas 16*a* and 16*b* can be terminated in a hub 18*a* and 18*b*, respectively, configured for coupling thereto a tip of a syringe, such that components contained in the syringe can be introduced into the cannulas 16*b* and 16*b* through the hubs 18*a* and 18*b*.

As shown, the syringes 20*a* and 20*b* coupled to the hubs 18*a* and 18*b*, receptively, can include a bridging member 23 coupling the plungers 22 thereof to one another, such that both plungers are operated simultaneously so that the components contained in the syringes 20*a* and 20*b* are introduced into the hubs 18*a* and 18*b* at the same time.

The medical applicator 10 can further include a lumen inlet 25 for receiving therein gas from an exterior source, for example, by coupling thereto an air tube. The lumen inlet 25 is in fluid communication with the tubular body 15 such that gas can be delivered, for example for atomization of the multicomponent medicament e.g. the curable liquid substance.

GENERAL DESCRIPTION

There is provided according to an aspect of the presently disclosed subject matter an addition to a medical applicator.

The medical applicator is configured for applying a multi-component medicament such as a curable liquid substance and includes a lumen inlet for receiving therein gas from an exterior source, and a tubular body for applying the curable liquid substance on a surface wherein the tubular body is in fluid communication with the lumen inlet. The addition can be configured to deliver powder to the surface. The addition comprising a turbulating unit configured for mixing the gas with a powder stored in a vial. The turbulating unit having an inlet port connectable to the exterior source, an outlet port connectable to the lumen inlet of the medical applicator and a spike member configured for being entered into the vial and having a first passage for providing fluid communication between the inlet port and the vial and a second passage for providing fluid communication between the vial and the outlet port. Whereby assembling the addition with the medical applicator enables delivery of the substance and the powder on the surface.

The delivery of the liquid substance and the powder to the surface can be carried out simultaneously. The delivery of the substance and the powder to the surface can be carried out sequentially. The delivery of the substance and the powder to the surface can be carried out alternatingly.

The second passage can be configured to allow a flow of gas homogeneously mixed with the powder.

The spike member can include a beveled tip configured for introducing the spike through a membrane covering the opening of the vial.

The gas can be a medical gas (e.g. air, $N_2$, $CO_2$ or other medical gases like oxygen), and the powder can be a medicament. The powder can comprise solid fibrinogen particles and/or solid thrombin particles.

The liquid substance can include at least a first component and a second component wherein the first component being activated by the second component.

The tubular body can contain a first channel for transferring therethrough the first component, a second channel for transferring therethrough the second component and a third channel for transferring therethrough the powder.

The applicator can comprise a first cannula hub for providing therethrough the first component and a second cannula hub for providing therethrough the second component.

The first component can comprise liquid fibrinogen, and the second component can comprise liquid thrombin.

The turbulating unit can be configured for sealing engagement with the opening of the vial.

The turbulating unit can be configured to homogeneously mix the powder with the gas.

The turbulating unit can be configured to form a mixture of the powder and the gas with a predetermined concentration of the powder in the gas.

The turbulating unit can be configured to form a mixture of the powder and the gas with a concentration of powder to gas ranging from 25 mg powder/liter of gas to 35 mg powder/liter of gas.

The addition can further comprise a first lumen configured for fluidly coupling the inlet port to the exterior source.

The addition can further comprise a second lumen configured for fluidly coupling the outlet port to the lumen inlet of the medical applicator.

The addition can further comprise a bypass lumen fluidly coupling the first lumen directly with said second lumen.

The addition can further comprise a valve coupled to the bypass lumen, the valve being configured to shift between a first position in which gas flow can be allowed between the exterior source and the vial whereby the powder can be mixed with the gas and a second position in which gas flow can be allowed between the exterior source and the bypass lumen whereby the gas flows directly to the lumen inlet.

According to a further aspect of the presently disclosed subject matter there is provided an applicator assembly comprising: at least one cannula hub for providing therethrough a liquid substance; a lumen inlet for receiving therein gas from an exterior source; and a turbulating unit configured for mixing the gas with a powder stored in a vial. The turbulating unit including an inlet port connectable to the exterior source; an outlet port connectable to the lumen inlet; and a spike member configured for being entered into the vial and having a first passage for providing gas communication between the inlet port and the vial and a second passage for providing fluid communication between the vial and the outlet port. The applicator assembly further comprising a tubular body for applying the liquid substance and the powder on a surface.

The applicator assembly can further comprise a first lumen fluidly coupling the inlet port to the exterior source.

The applicator assembly can further comprise a second lumen fluidly coupling the outlet port to the lumen inlet.

The applicator assembly can further comprise a bypass lumen fluidly coupling the first lumen directly with the second lumen or with the lumen inlet.

The applicator assembly can further comprise a valve coupled to the bypass lumen and the valve being configured to shift between a first position in which gas flow can be allowed between the exterior source and the vial whereby the powder can be mixed with the gas, and a second position in which gas flow is allowed between the exterior source and the bypass lumen whereby the gas flows directly to the lumen inlet.

The substance can include a first liquid component and a second liquid component wherein said first component being activated by the second component and wherein the assembly can include a first cannula for transferring therethrough the first component, a second cannula for transferring therethrough the second component.

The tubular body can contain a first channel for transferring therethrough the first component, a second channel for transferring therethrough the second component and a third channel for transferring therethrough the gas and powder.

According to yet a further aspect of the presently disclosed subject matter there is provided a method for applying a powder and a liquid curable substance on a surface, by utilizing an applicator assembly as described above. The method comprising: providing pressurized gas into a vial having the powder stored therein, such that a mixture of the gas and the powder can be formed; transferring the mixture towards the lumen inlet; applying with the tubular body the mixture on the surface; providing the liquid substance into the cannula hub; and applying with the tubular body the substance onto the surface.

The pressure of the gas delivered to the vial and/or to the medical applicator can be in the range of 5 to 30 psi.

The step of applying the substance and the step of applying mixture can be carried out simultaneously.

The step of applying the substance and the step of applying the mixture can be carried out sequentially.

The step of applying the mixture and the step of applying the substance can be carried out alternatingly.

The substance can be formed by a first liquid component and a second liquid component wherein the first component can be activated by the second component.

The surface can be a moist surface, such as a bleeding wound, a leaking defect, in a subject. In another embodiment of the invention, the tissue is moist from a fluid which is fibrinogen free. The term "fibrinogen free" refers, for example, to a fibrinogen concentration of lower than 1.5 g/L.

The term "moist surface" e.g. a moist tissue refers to a wet tissue and includes e.g. mucosa, mucosa tissue and other moist tissue.

The device can be used to stop bleeding, to seal leaks, to join structures, to enhance healing, and to reduce adhesions.

As used herein, the term "defect" refers to a tear, aperture, bore, fissure, puncture, hole, crack, opening, slit, gap, perforation, fracture, puncture or rupture, leak e.g. in a tissue. E.g. the defect can be formed following an anastomosis procedure. The defect can be congenital e.g. hernia; a condition resulting from body related pathology e.g. seroma, hernia, infection, inflammation; formed after surgery, suturing and/or stapling; or a condition resulting from a non-body factor e.g. accidents, injuries.

The term "leak" refers to the escape or pass of a substance e.g. fluid, viscous material and/or air e.g. through a tear, aperture, bore, fissure, puncture, hole, crack, opening, slit, gap, perforation, fracture, puncture or rupture in a tissue.

The term "anastomosis" typically refers to a surgical procedure which is used to reconnect two or more sections of an organ or tissue. The procedure can be used following sectioning of the urinary tract (urethra), throat (esophagus), or in bowel surgery. The procedure can also be used following the excision of a diseased tissue (such as inflamed, cancerous or otherwise pathological tissue e.g. ulcerative disease).

The wet surface can be a surface of a body part of a patient e.g. any tissue that contains liquids or air. The term "surface" includes, but is not limited to, the genital area, including the uterus, vagina and ovaries; the lungs; the anus; the spleen; the liver; the dura mater; the renal; the esophagus; the stomach; the pancreas; the pancreatic duct; the gall bladder; the bile duct; the intestine (including the small intestine and the large intestine); and the cardiac muscle. The surface can be a bleeding or a non-bleeding site. In one embodiment of the invention, the surface is a non-bleeding site. In another embodiment of the invention, the surface is wet from a fluid which is coagulation factor free (e.g. free of fibrinogen). The surface can also be any surface e.g. a working surface, a surface of a prosthetic device.

As used herein, the term "curable" in connection with a liquid composition, refers to a composition which can undergo an interaction between its components leading to an increase in viscosity of the composition. Such interactions include polymerization and/or cross-linking of components, achieved by means that include, but are not limited to, use of activating agents such as catalysts, or physical activators such as heat, radiation e.g. ultraviolet radiation, electron beams, or combinations thereof.

In some embodiments, the curable liquid composition comprises at least two components. In some embodiments, a first of at least two components is activated by a second of at least two components. In some such embodiments, the first component comprises fibrinogen. In some such embodiments comprising fibrinogen, the second component, for activation of fibrinogen, comprises thrombin.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
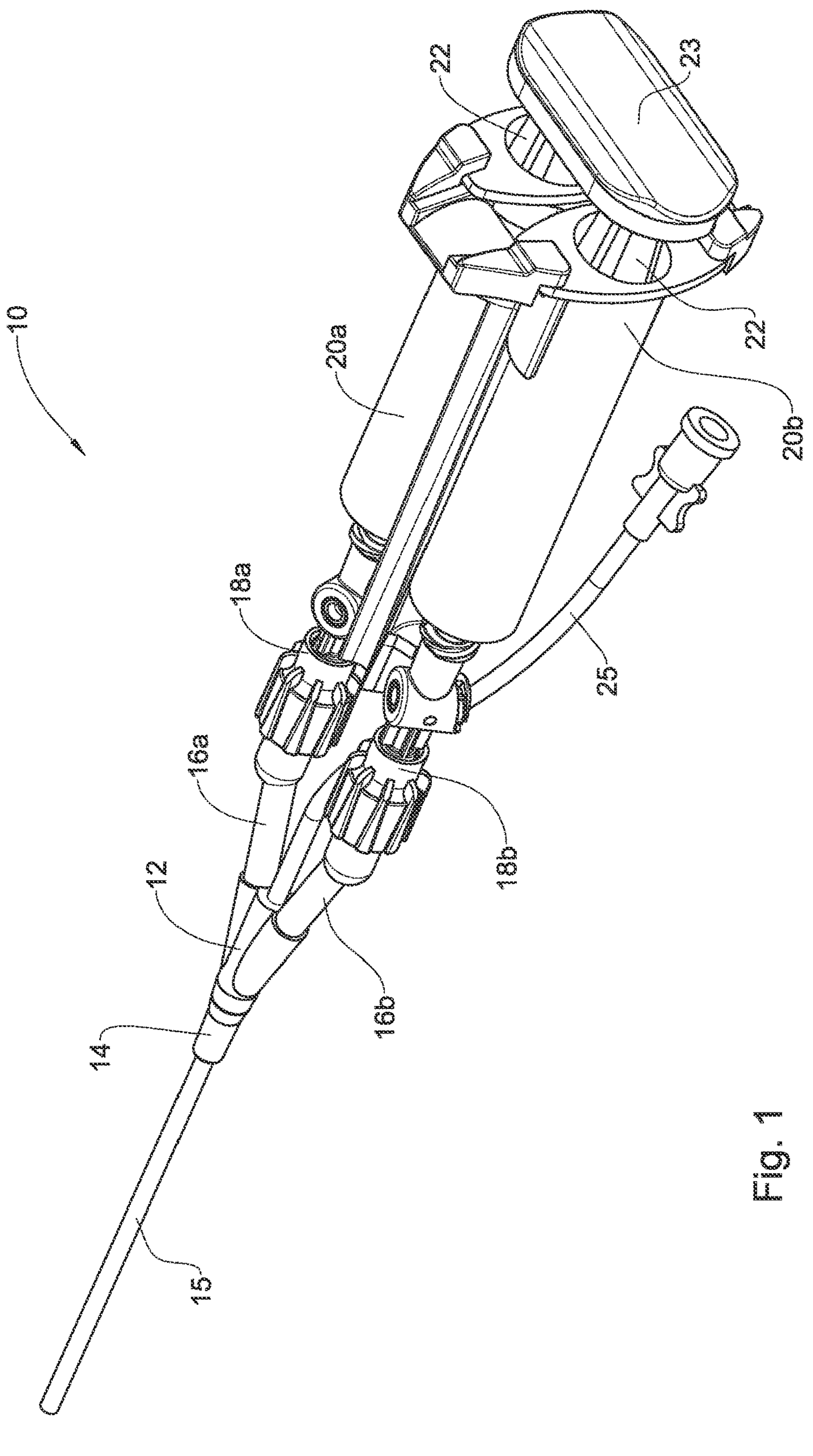
FIG. 1 is a perspective view of a known medical applicator configured for applying a curable liquid substance on a surface.

As discussed hereinabove in the Background Section FIG. 1 shows a known medical applicator 10 configured for applying a multicomponent medicament on a surface, for example, a curable liquid substance, including two or more components. The medical applicator 10 includes two or more cannulas 16*a* and 16*b* into which the components can be fed and a tubular body 15 for applying thereof on a surface.

Figure 2:
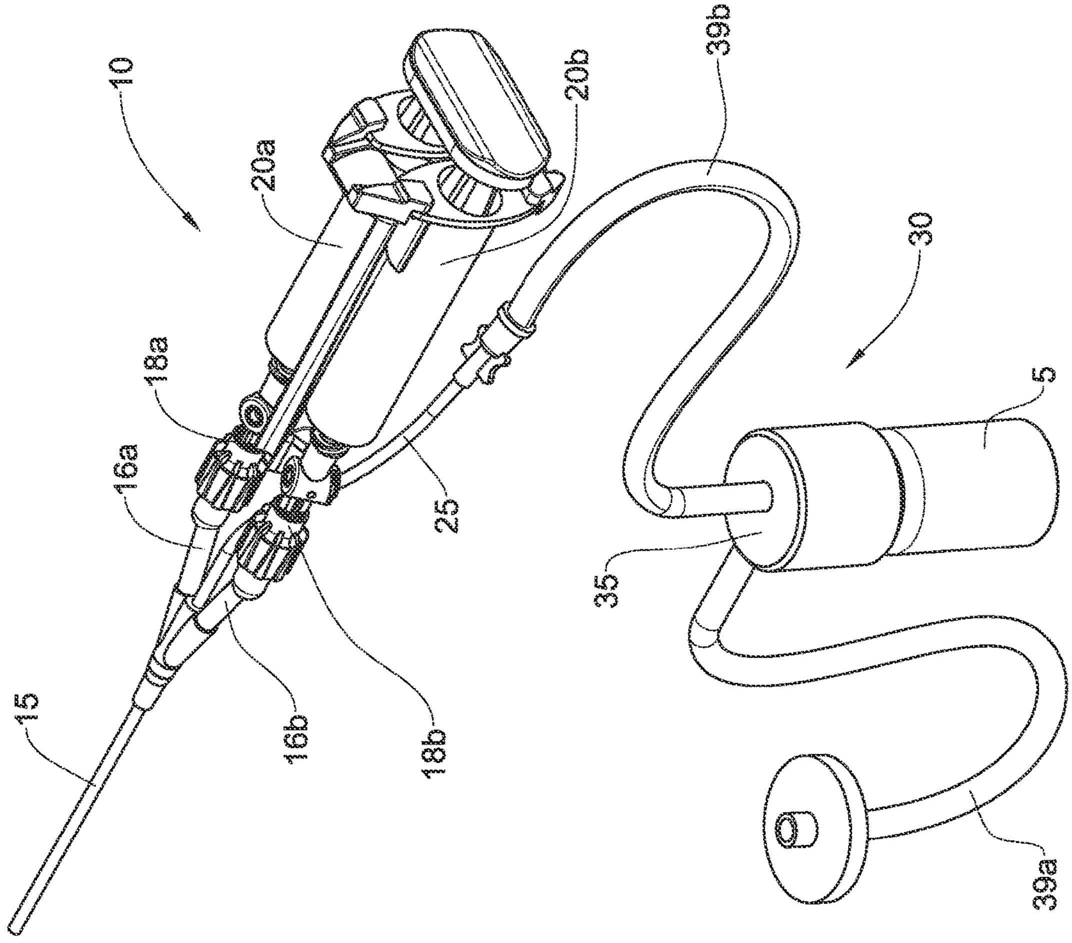
FIG. 2 is a perspective view of an addition according to an example of the presently disclosed subject matter coupled to the medical applicator of FIG. 1.
Figure 3:
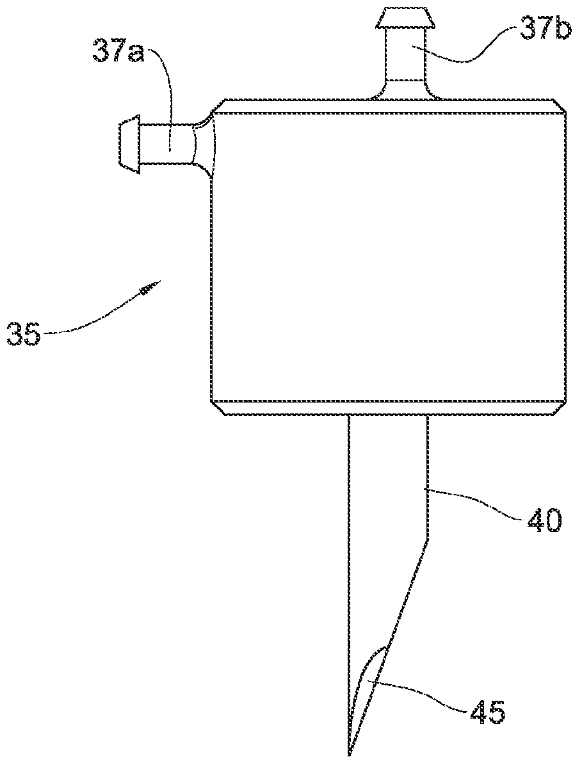
FIG. 3 is a side view of a turbulating unit according to an example of the presently disclosed subject matter.

According to an example the medical applicator 10 further includes a lumen inlet 25 for receiving therein gas from an exterior source. FIG. 2 shows an addition 30 to a medical applicator 10 configured for providing a mixture of a gas and a powdered component to the medical applicator. The addition 30 comprising a turbulating unit 35 configured for mixing gas, such as a medical gas, with a powder stored in a vial 5. The turbulating unit 35 includes an inlet port 37*a* (shown in FIG. 3) connectable to the exterior source, such as a gas tank (not shown), and an outlet port 37*b* connectable to the lumen inlet 25 of the medical applicator 10.

In addition, the turbulating unit 35 can further include a spike member 40 configured for being entered into a vial, and can include a beveled tip 45 configured for introducing the spike through a membrane covering the opening of the vial 5.

The spike member 40 includes a first passage 42*a* for providing fluid communication between the inlet port 37*a* and the inside volume of the vial 5 and a second passage 42*b* for providing fluid communication between the inside volume of the vial 5 and the outlet port 37*b*.

The turbulating unit 35 is configured to form a mixture of the powder stored in the vial 5 and the gas with a predetermined concentration thereof. That is to say, the amount and rate of gas introduced to the vial is set in accordance with the required concentration of the mixture of the powder and the gas. It is appreciated that the concentration level of the mixture may depend on various parameters such as the specific gravity of the gas, the pressure in the exterior source, the properties of the powder stored inside the vial 5, etc. For example, the pressure of the gas delivered to the vial can be 5 to 30 psi and/or the volumetric flow rate can be set to 2-7 liter gas per minute. In addition, it is appreciated that the diameter of the first passage 42*a* is configured such that the gas introduced therethrough homogeneously mixes the powder inside the vial 5.

The turbulating unit 35 can be further configured for sealing engagement with the opening of the vial 5, such that the desired pressure inside the vial 5 is maintained while the gas, or other fluids are introduced therein.

According to an example the addition 30 further includes a first lumen 39*a* configured for fluidly coupling the inlet port 37*a* to the exterior source of gas, such as to the gas tank. According to another example, the addition 30 can include a second lumen 39*b* configured for fluidly coupling the outlet port 37*b* to the lumen inlet 25 of the medical applicator 10. This way the addition can be assembled together with an applicator of any kind, that is to say the second lumen 39*b* can serve as an adaptor between the outlet port 37*b* and the lumen inlet 25 of the medical applicator.

According to an example the second lumen 39*b* can be configured to allow disposing the turbulating unit 35 and the vial 5 remotely from the applicator facilitating thereby the use of the applicator. This way, the applicator 10 can be operated by one medical attendant while the addition 30 can be operated by another medical attendant.

Utilizing the applicator 10 with the addition 30 allows applying a curable liquid substance on a surface, for example on a tissue for holding together two adjacent tissue portions, such as following a surgery, and a powder such as solid fibrinogen and/or solid thrombin, e.g. as disclosed in WO 2011092694, or any other powder which can facilitate treatment.

In addition the gas delivered from the exterior source and introduced into the vial can be a medical gas, and wherein the powder can be a medicament such as a medicament including solid fibrinogen particles and/or solid thrombin particles.

The curable liquid substance applied by the applicator can include a first component contained within the first syringe 20*a* and a second component contained within the second syringe 20*b*. The first component can be such which interacts with the second component, for example the first component can include fibrinogen, and the second component can include thrombin. Examples of the two components include, but are not limited to, fibrinogen and thrombin, alginate and calcium, pectin and calcium a synthetic sealant such as acrylates, cyanoacrylates, and polyethylene glycol (PEG) polymers with their crosslinkers; and a semisynthetic sealant e.g. made from a combination of biological and synthetic materials such as gelatin-formaldehyde-resorcinol (GFR) glue, albumin and glutaraldehyde.

In one embodiment of the invention, the two components of the substance are fibrinogen and thrombin. In such an embodiment, when the two liquid components are mixed polymerization process is activated and application of the sealant is advantageously carried out without delay before resistance to flow becomes excessive. This way, the first and second components can be in a liquid (e.g. aqueous) form when stored separately, and can cure when mixed together, or engage one another. Thus, the first component can be applied on the surface through the first cannula hub 18*a*, while the second component is applied through the second cannula hub 18*b*.

Figure 6:
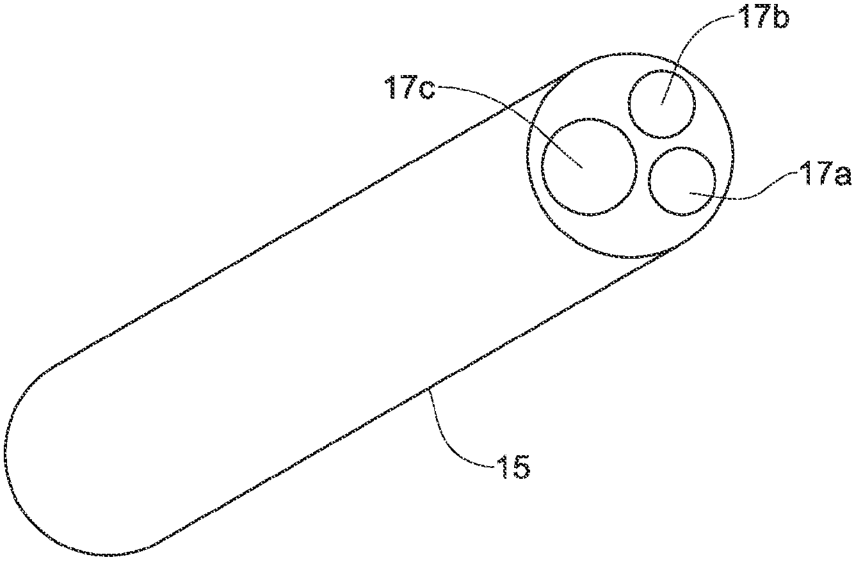
FIG. 6 is a sectional view of a tubular body according to an example of the presently disclosed subject matter.

As shown in FIG. 6 in order to preclude undesirable activation of the first component by the second component inside the tubular body 15, the latter can contain a first channel 17*a* for transferring therethrough the first component, a second channel 17*b* for transferring therethrough the second component. Thus, the activation of the component takes place outside the tubular body 15, for example on the treated surface e.g. as in WO2012168933A2[1] and as described in U.S. Pat. No. 8,403,882. The tubular body 15 can further include a third channel 17*c* for transferring therethrough the mixture of the powder and the gas.

Alternatively, the two components can be mixed within the device prior to exiting the tip of the tubular body. In that case the tubular body can be structured as described in WO10095128A2, U.S. Patent Application 2007/0191781 A1.

According to the presently disclosed subject matter the operator can provide pressurized gas into the vial through the first lumen 39*a* and inlet port 37*a* of the turbulating unit 35. The pressurized gas causes turbulence inside the vial resulting in a mixture of the powder therewith. Due to the continuous flow of pressurized gas the mixture is urged into the outlet port 37*b* and the second lumen 39*b* towards the lumen inlet 25 of the applicator 10. The mixture can then be applied with the tubular body 15 on the surface e.g. the surface to be treated.

At this point the plungers 22 of the syringes 20*a* and 20*b* can be activated by pushing the bridging member 23 so as to urge the first and the second components towards the tubular body 15, through the first and second hubs 18*a* and 18*b*, respectively.

The components can then be applied at least partially on the applied powder through the tubular body 15 and onto the surface, resulting in the formation of the curable substance.

It is appreciated that delivery of the components of the curable substance and the powder on the surface can be carried out simultaneously, sequentially or alternatingly.

According to an example, the components of the curable substance can be delivered through a first and second channels 17*a* and 17*b* of the tubular body (FIG. 6), while the powder can be delivered through a third channel 17*c*, such that the powder does not engage the components of the curable substance or residue thereof, if so desired.

In another example, the powder can be delivered through the same channel as that through which the components are delivered. In the latter case the powder can be delivered before the components while the channels 17*a* and 17*b* are still empty of any component residue.

It is appreciated that in the event where all the powder from the vial is delivered, gas from the external source can be further delivered through the tubular body. This way the gas can be utilized for cleaning the channels of the tubular body of any component residue.

In addition, if the tubular body of FIG. 6 is utilized, once the vial is empty of powder, gas can be delivered through the empty vial, towards the third channel 17*c* of the tubular body 15 while the first and second components are delivered through the first and second channels 17*a* and 17*b* respectively. This way the gas can be used for atomization of the components, such that the components are sprayed over the treated surface.

According to an example, a bypass lumen (not shown) can be provided. The bypass lumen allows the operator to provide gas form the exterior source directly to the medical applicator 10 without entering into the vial and/or mixing thereof with the powder inside the vial 5. For example such bypass lumen can be placed between the first lumen 39*a* and the second lumen 39*b*. This example is explained in more detail hereinafter with reference to FIG. 7.

Figure 7:
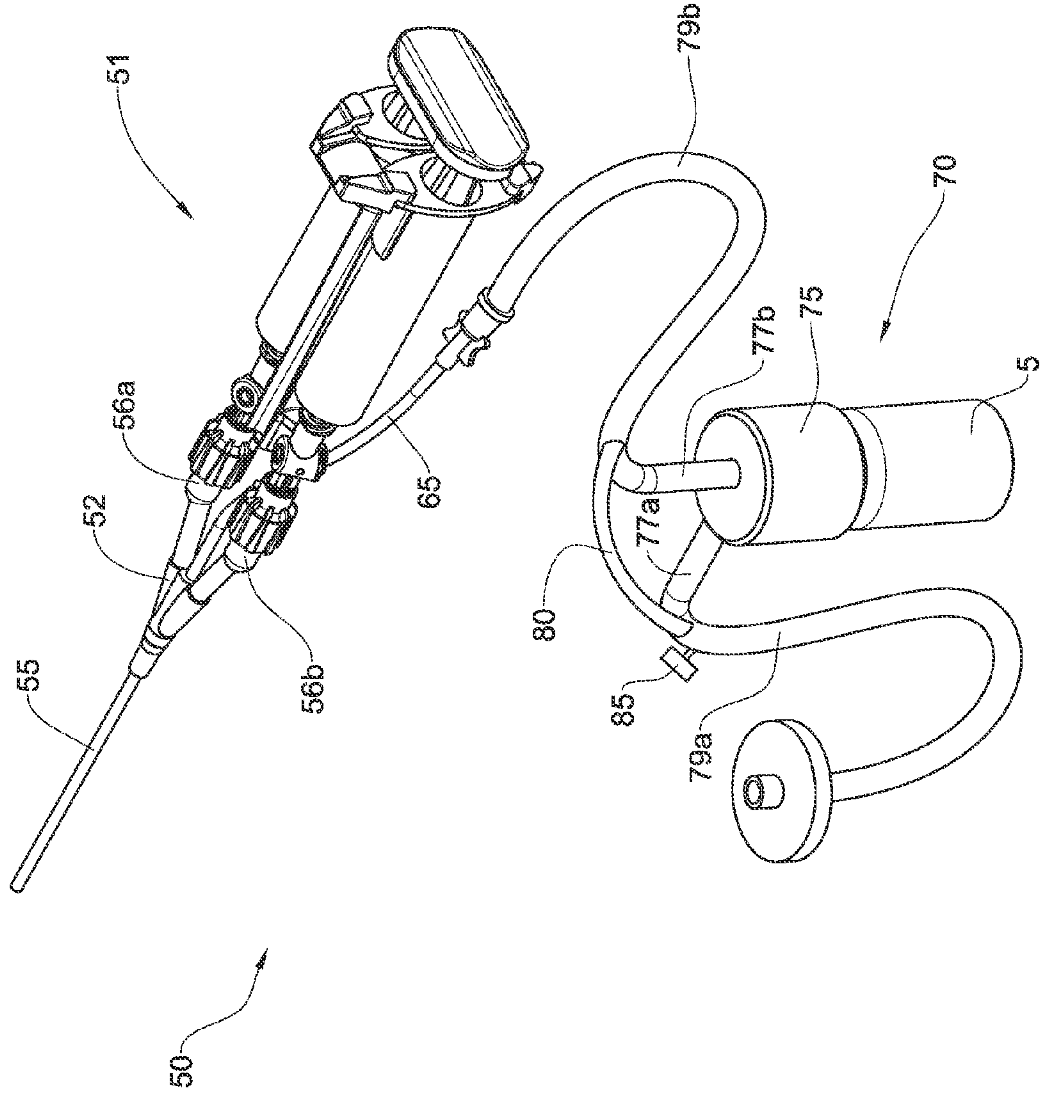
FIG. 7 is an applicator assembly according to an example of the presently disclosed subject matter.

Reference is now made to FIG. 7, the presently disclosed subject matter further provides an applicator assembly 50 having a medical applicator 51, substantially the same as the applicator of FIG. 1 and having a headpiece 52 including a tubular body 55, two or more cannulas 56*a* and 56*b* into which the components can be fed, and a lumen inlet 65 for receiving therein gas from an exterior source. The applicator assembly 50 further includes an addition 70 substantially the same as the addition 30 of the previous examples and comprising a turbulating unit 75 configured for mixing gas, such as a medical gas, with a powder stored in a vial 5. The turbulating unit 75 includes an inlet port 77*a* connectable to the exterior source e.g. via a first lumen 79*a*, and an outlet port 77*b* connectable to the lumen inlet 65 of the medical applicator 51 e.g. via a second lumen 79*b*.

According to this example, the assembly 50 further includes a bypass lumen 80 fluidly coupling the first lumen 79*a* directly with the second lumen 79*b*. The bypass lumen 80 allows the operator to provide the gas form the exterior source directly to the medical applicator 51 without entering into the vial and/or mixing thereof with the powder inside the vial 5.

The bypass lumen 80 can be further provided with a valve 85 coupled thereto. In one embodiment, valve 85 allows gas flow from the exterior source, to be apportioned from the first lumen 79*a* into the inlet port 77*a* and the bypass lumen 80. The valve 85 can be configured to shift between a first position and a second position. In the first position, gas flow is allowed between the exterior source and the vial 5, through the first lumen 79*a* and into inlet port 77*a*, whereby the powder is mixed with the gas. In the second position, a direct gas flow is allowed between the exterior source and the lumen inlet 65 of the medical applicator 51 through the bypass lumen 80. Thus, in the second position, gas from the exterior source can be fed into the medical applicator, without entering into the vial and/or mixing thereof with the powder inside the vial 5.

Figure 4:
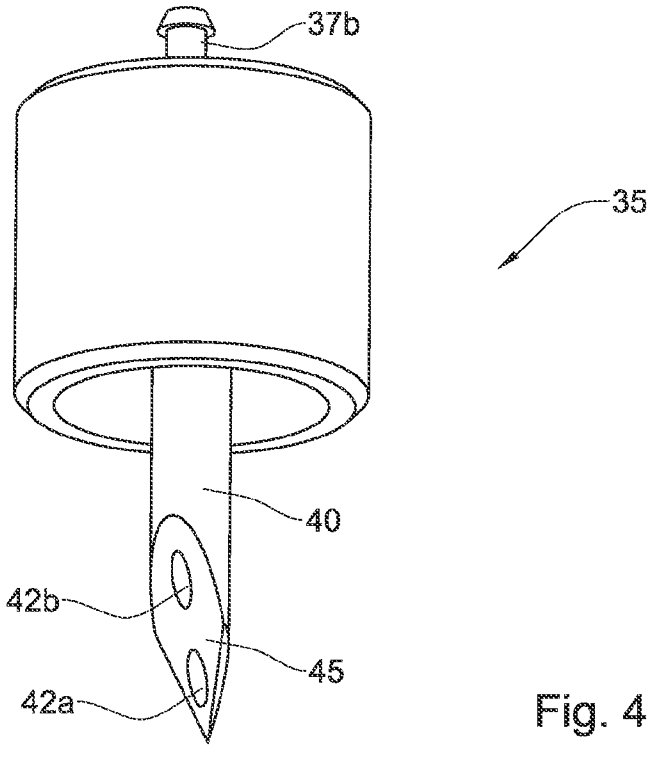
FIG. 4 is bottom view of a turbulating unit of FIG. 3.
Figure 5:
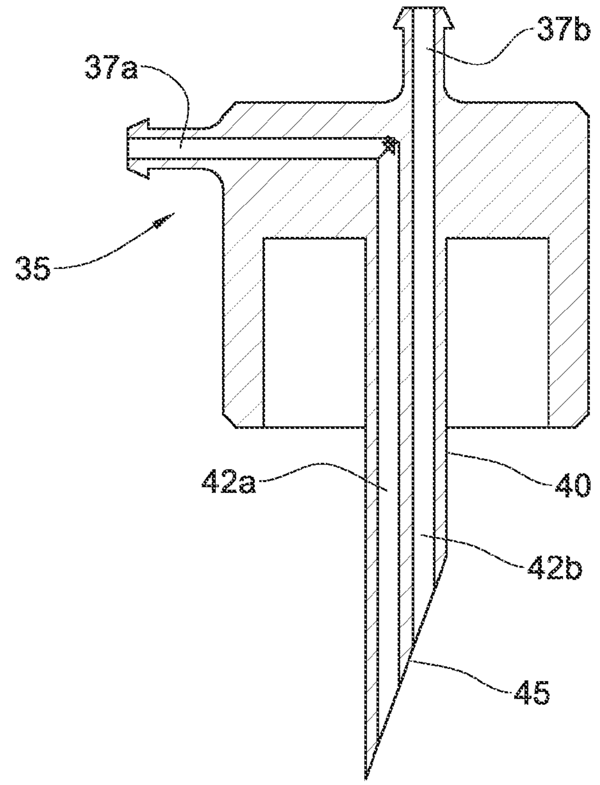
FIG. 5 is sectional view of the turbulating unit of FIG. 3.

Referring back to FIGS. 3 and 4, the spike member 40 includes a first passage 42*a* for providing fluid communication between the inlet port 37*a* and the inside volume of the vial 5 and a second passage 42*b* for providing fluid communication between the inside volume of the vial 5 and the outlet port 37*b*. Passage 42*a* can be oriented laterally with respect to the spike member 40. Lateral orientation enables greater separation between the first passage 42*a* and the second passage 42*b* which thereby allows for more efficient transfer of powder to the second passage 42*b*. Further, the lateral orientation can be angled such that gas inflow through first passage 42*a* creates a swirling effect within vial 5 to more efficiently engage the powder with the gas such that a more homogenous mixture is formed.

Referring again to FIG. 7, valve 85 can be configured to allow for proportional distribution of the gas inflow from first lumen 79*a* such that a portion of the gas flow passes through first passage 42*a* and a second portion passes through bypass lumen 80. Proportional distribution enables greater control over the concentration of powder delivered through second lumen 79*b* and ultimately to the tissue surface. This effect may also be achieved by the addition of a variable restrictor element within the bypass lumen 80 or between valve 85 and inlet port 77*a*. This feature can be used to adjust for variation in available gas pressure to enable more predictable delivery of powder volume. Adjustment positions may be pre-calibrated and labeled to correspond to various gas pressure supplies.

The presently disclosed subject matter thus provides an addition to a medical applicator (10), the medical applicator configured for applying a curable liquid substance, and including a lumen inlet (25) for receiving therein gas from an exterior source, and a tubular body (15) for applying the curable liquid substance on a surface, wherein the tubular body is in fluid communication with the lumen inlet, the addition comprising a turbulating unit (35) configured for mixing the gas with a powder stored in a vial (5). The turbulating unit having: an inlet port (37*a*) connectable to the exterior source, an outlet port (37*b*) connectable to the lumen inlet (25) of the medical applicator; and a spike member (40) configured for being entered into the vial and having a first passage (42*a*) for providing fluid communication between the inlet port (37*a*) and the vial (5), and a second passage (42*b*) for providing fluid communication between the vial (5) and the outlet port (37*b*). Whereby assembling the addition with the medical applicator enables delivery of the substance and the powder on a surface.

The second passage (42*b*) can be configured to allow a flow of the gas homogeneously mixed with the powder.

The spike member (40) can include a beveled tip (45) configured for introducing the spike through a membrane covering the opening of the vial.

The applicator can comprise a first cannula hub (18*a*) for providing therethrough the first component and a second cannula hub (18*b*) for providing therethrough the second component.

The turbulating unit (35) can be configured for sealing engagement with the opening of the vial.

The turbulating unit (35) can be configured to homogeneously mix the powder with the gas.

The turbulating unit (35) can be configured to form a mixture of the powder and the gas with a predetermined concentration of the powder in the gas.

The addition can further comprise a first lumen (39*a*) configured for fluidly coupling the inlet port (37*a*) to the exterior source.

The addition can further comprise a second lumen (39*b*) configured for fluidly coupling the outlet port (37*b*) to the lumen inlet (25) of the medical applicator.

The addition can further comprise a bypass lumen (80) fluidly coupling the first lumen (39*a*) directly with the second lumen (39*b*).

The addition can further comprise a valve coupled to the bypass lumen, the valve being configured to shift between a first position in which gas flow is allowed between the exterior source and the vial (5) whereby the powder is mixed with the gas, and a second position in which gas flow is allowed between the exterior source and the bypass lumen whereby the gas flows directly to the lumen inlet (25).

The applicator is capable of applying, liquid solution in dripping form, atomized liquid solution with gas, powder with gas, and combinations thereof.

The presently disclosed subject matter further provides an applicator assembly (50) comprising: at least one cannula hub (18) for providing therethrough a curable liquid substance; a lumen inlet (25) for receiving therein gas from an exterior source; and a turbulating unit (35) configured for mixing the gas with a powder stored in a vial (5), the turbulating unit including an inlet port (37*a*) connectable to the exterior source; an outlet port (37*b*) connectable to the lumen inlet (25); and a spike member (40 FIG. 3) configured for being entered into the vial and having a first passage (42*a*) for providing fluid communication between the inlet port (37*a*) and the vial (5) and a second passage (42*b*) for providing fluid communication between the vial (5) and the outlet port (37*b*); and a tubular body (15) for applying the substance and a mixture of the gas and the powder on a surface.

The applicator assembly can further comprise a first lumen (39*a* FIG. 2) fluidly coupling the inlet port (37*a*) to the exterior source.

The applicator assembly can further comprise a second lumen (39*b*) fluidly coupling the outlet port (37*b* FIG. 2) to the lumen inlet (25).

The applicator assembly can further comprise a bypass lumen (80, FIG. 7) fluidly coupling the first lumen directly with the second lumen.

The applicator assembly can further comprise a valve (85) coupled to the bypass lumen the valve being configured to shift between a first position in which gas flow is allowed between the exterior source and the vial (5) whereby the powder is mixed with the gas, and a second position in which gas flow is allowed between the exterior source and the bypass lumen whereby the gas flows directly to the lumen inlet.

Those skilled in the art to which the presently disclosed subject matter pertains will readily appreciate that numerous changes, variations, and modifications can be made without departing from the scope of the invention, mutatis mutandis.

The invention claimed is:

1. An applicator assembly comprising: a medical applicator configured for applying a curable liquid substance, and an addition to the a medical applicator, the medical applicator including at least one cannula hub for providing therethrough a curable liquid substance, a lumen inlet for receiving therein gas from an exterior source, and a tubular body for applying the curable liquid substance on a surface, wherein the tubular body is in fluid communication with the lumen inlet, the addition comprising a turbulating unit configured for mixing said gas with a powder stored in a vial, the turbulating unit having:

an inlet port connectable to the exterior source;

an outlet port connectable to the lumen inlet of the medical applicator; and a spike member configured for being entered into the vial and having a first passage for providing fluid communication between said inlet port and the vial, and a second passage for providing fluid communication between the vial and said outlet port;

wherein the delivery path of powder is through the outlet port, lumen inlet, and tubular body, and wherein the delivery path of the curable liquid substance is through the cannula hub and tubular body whereby the assembly enables delivery of the curable liquid substance and the powder on the surface through the tubular body.

2. The applicator assembly of claim 1, wherein said spike member includes a beveled tip configured for introducing said spike through a membrane covering the opening of the vial.

3. The applicator assembly of claim 1, wherein said gas is a medical gas, and wherein said powder is a medicament.

4. The applicator assembly of claim 1, wherein said powder comprises solid fibrinogen particles and/or solid thrombin particles.

5. The applicator assembly of claim 1, wherein the substance includes at least a first component and a second component, wherein said first component being activated by said second component.

6. The applicator assembly of claim 5, wherein the tubular body contains a first channel for transferring therethrough said first component, a second channel for transferring therethrough said second component, and a third channel for transferring therethrough said powder.

7. The applicator assembly of claim 5, wherein the applicator comprises a first cannula hub for providing therethrough said first component and a second cannula hub for providing therethrough said second component.

8. The applicator assembly of claim 5, wherein said first component comprises liquid fibrinogen, and said second component comprises liquid thrombin.

9. The applicator assembly of claim 1, further comprising a bypass lumen fluidly coupling said first lumen directly with a second lumen.

10. The applicator assembly of claim 9 further comprising a valve coupled to said bypass lumen, said valve being configured to shift between a first position in which fluid flow is allowed between said exterior source and said vial whereby said powder is mixed with said gas, and a second position in which fluid flow is allowed between said exterior source and said bypass lumen whereby said gas flows directly to said lumen inlet.

11. The applicator assembly of claim 10, wherein said valve allows gas flow from said exterior source, to be apportioned from said first lumen into said inlet port and into said bypass lumen.

* * * * *